(12) United States Patent
Connolly et al.

(10) Patent No.: US 10,252,981 B2
(45) Date of Patent: Apr. 9, 2019

(54) METHODS OF SYNTHESIS OF (1R,2R,5R)-5-AMINO-2-METHYLCYCLOHEXANOL HYDROCHLORIDE AND INTERMEDIATES USEFUL THEREIN

(71) Applicant: Celgene Corporation, Summit, NJ (US)

(72) Inventors: Terrence Joseph Connolly, Warwick, NY (US); Hon-Wah Man, Princeton, NJ (US); Periyandi Nagarajan, Hyderabad (IN); Chinnapillai Rajendiran, Hyderabad (IN); Jasti Venkateswarlu, Hyderabad (IN)

(73) Assignee: Celgene Corporation, Summit, NJ (US)

( * ) Notice: Subject to any disclaimer, the term of this patent is extended or adjusted under 35 U.S.C. 154(b) by 0 days.

(21) Appl. No.: 15/746,853

(22) PCT Filed: Jul. 22, 2016

(86) PCT No.: PCT/US2016/043511
§ 371 (c)(1),
(2) Date: Jan. 23, 2018

(87) PCT Pub. No.: WO2017/019487
PCT Pub. Date: Feb. 2, 2017

(65) Prior Publication Data
US 2018/0215700 A1    Aug. 2, 2018

Related U.S. Application Data

(60) Provisional application No. 62/196,363, filed on Jul. 24, 2015.

(51) Int. Cl.
C07C 51/09 (2006.01)
C07C 61/22 (2006.01)
(Continued)

(52) U.S. Cl.
CPC ............ *C07C 213/02* (2013.01); *C07C 51/09* (2013.01); *C07C 67/347* (2013.01);
(Continued)

(58) Field of Classification Search
None
See application file for complete search history.

(56) References Cited

U.S. PATENT DOCUMENTS

| 2,859,239 A | 11/1958 | Trapp et al. |
| 3,845,055 A | 10/1974 | Hoegerle et al. |

(Continued)

FOREIGN PATENT DOCUMENTS

| EP | 0 520 419 | 12/1992 |
| EP | 1 184 376 | 3/2002 |

(Continued)

OTHER PUBLICATIONS

Berkessel ("Enantiomerically Pure Isophorone Diamine [3-(Aminomethyl)-3,5,5-trimethylcyclohexylamine]: A Chiral 1,4-Diamine Building Block Made Available on Large Scale" J. Org. Chem., 2006, vo. 71, p. 9312-9318) (Year: 2006).*

(Continued)

*Primary Examiner* — Amy C Bonaparte
(74) *Attorney, Agent, or Firm* — Jones Day

(57) ABSTRACT

Provided herein are methods and intermediates for making (1R,2R,5R)-5-amino-2-methylcyclohexanol hydrochloride, which are useful for the preparation of compounds useful for the treatment of a disease, disorder, or condition associated with the JNK pathway.

16 Claims, 4 Drawing Sheets

(51) Int. Cl.

| | | |
|---|---|---|
| C07C 209/58 | (2006.01) | |
| C07C 209/88 | (2006.01) | |
| C07C 211/40 | (2006.01) | |
| C07C 213/02 | (2006.01) | |
| C07C 215/44 | (2006.01) | |
| C07C 231/02 | (2006.01) | |
| C07C 233/58 | (2006.01) | |
| C07C 269/04 | (2006.01) | |
| C07C 269/06 | (2006.01) | |
| C07C 271/24 | (2006.01) | |
| C07C 67/347 | (2006.01) | |
| C07C 69/608 | (2006.01) | |

(52) U.S. Cl.
CPC .......... *C07C 209/58* (2013.01); *C07C 209/88* (2013.01); *C07C 211/40* (2013.01); *C07C 231/02* (2013.01); *C07C 269/04* (2013.01); *C07C 269/06* (2013.01); *C07B 2200/07* (2013.01); *C07C 2601/14* (2017.05); *C07C 2601/16* (2017.05)

(56) References Cited

U.S. PATENT DOCUMENTS

| | | | |
|---|---|---|---|
| 5,763,647 A * | 6/1998 | Ohtani | C07C 209/88 562/401 |
| 6,432,963 B1 | 8/2002 | Hisamichi et al. | |
| 7,169,798 B2 | 1/2007 | Green et al. | |
| 7,358,384 B2 * | 4/2008 | Morii | C07C 67/52 560/180 |
| 7,449,456 B2 | 11/2008 | Nagashima et al. | |
| 7,517,886 B2 | 4/2009 | Singh et al. | |
| 7,524,849 B2 | 4/2009 | Zhang et al. | |
| 7,589,200 B2 | 9/2009 | Singh et al. | |
| 7,601,714 B2 | 10/2009 | Barbosa et al. | |
| 7,718,653 B2 | 5/2010 | Barlaam et al. | |
| 7,893,074 B2 | 2/2011 | Garcia-Echeverria et al. | |
| 7,956,060 B2 | 6/2011 | Arai et al. | |
| 8,012,959 B2 | 9/2011 | Nagashima et al. | |
| 8,044,044 B2 | 10/2011 | Hubschwerlen et al. | |
| 8,188,113 B2 | 5/2012 | Flynn et al. | |
| 8,222,447 B2 | 7/2012 | Mang et al. | |
| 8,338,439 B2 | 12/2012 | Sing et al. | |
| 8,513,242 B2 | 8/2013 | Chiang et al. | |
| 8,519,129 B2 | 8/2013 | Marsilje et al. | |
| 8,580,805 B2 | 11/2013 | Maehr | |
| 8,853,230 B2 | 10/2014 | Bauer et al. | |
| 8,969,336 B2 | 3/2015 | Shimada et al. | |
| 9,139,534 B2 | 9/2015 | Bennett et al. | |
| 9,365,524 B2 | 6/2016 | Man et al. | |
| 9,512,124 B2 | 12/2016 | Alexander et al. | |
| 9,513,297 B2 | 12/2016 | Horan et al. | |
| 9,556,126 B2 | 1/2017 | Papa et al. | |
| 9,701,643 B2 | 7/2017 | Bennett et al. | |
| 9,796,685 B2 | 10/2017 | Boersen et al. | |
| 9,814,713 B2 | 11/2017 | Man et al. | |
| 2008/0139531 A1 | 6/2008 | Yanni et al. | |
| 2009/0036440 A1 | 2/2009 | Barlaam et al. | |
| 2010/0029623 A1 | 2/2010 | Hubschwerlen et al. | |
| 2011/0159019 A1 | 1/2011 | Tanaka et al. | |
| 2011/0130415 A1 | 6/2011 | Singh et al. | |
| 2013/0029987 A1 | 1/2013 | Bennett et al. | |
| 2013/0172562 A1 * | 7/2013 | Meek | B01J 21/18 546/185 |
| 2015/0210650 A1 * | 7/2015 | Ferretti | C07D 239/48 514/275 |
| 2016/0096841 A1 | 4/2016 | Alexander et al. | |
| 2016/0168105 A1 | 6/2016 | Boersen et al. | |
| 2017/0267647 A1 | 9/2017 | Delgado et al. | |
| 2018/0009765 A1 | 1/2018 | Boersen et al. | |
| 2018/0022710 A1 | 1/2018 | Man et al. | |
| 2018/0028534 A1 | 2/2018 | Man et al. | |

FOREIGN PATENT DOCUMENTS

| | | |
|---|---|---|
| EP | 1 518 855 | 3/2005 |
| JP | 2006/124387 | 5/2006 |
| WO | WO 1999/031073 | 6/1993 |
| WO | WO 2000/012485 | 3/2000 |
| WO | WO 2000/076980 | 12/2000 |
| WO | WO 2003/063794 | 8/2003 |
| WO | WO 2003/078404 | 9/2003 |
| WO | WO 2003/082855 | 9/2003 |
| WO | WO 2004/014382 | 2/2004 |
| WO | WO 2004/054617 | 7/2004 |
| WO | WO 2004/002964 | 8/2004 |
| WO | WO 2004/065378 | 8/2004 |
| WO | WO 2004/067516 | 8/2004 |
| WO | WO 2005/095382 | 10/2005 |
| WO | WO 2006/027377 | 3/2006 |
| WO | WO 2006/027378 | 3/2006 |
| WO | WO 2006/035069 | 4/2006 |
| WO | WO 2006/091737 | 8/2006 |
| WO | WO 2006/099231 | 9/2006 |
| WO | WO 2007/032445 | 3/2007 |
| WO | WO 2008/009458 | 1/2008 |
| WO | WO 2008/034008 | 3/2008 |
| WO | WO 2008/129380 | 10/2008 |
| WO | WO 2009/012421 | 1/2009 |
| WO | WO 2009/131687 | 10/2009 |
| WO | WO 2009/132980 | 11/2009 |
| WO | WO 2009/136995 | 11/2009 |
| WO | WO 2009/143389 | 11/2009 |
| WO | WO 2009/145856 | 12/2009 |
| WO | WO 2009/158571 | 12/2009 |
| WO | WO 2010/024430 | 3/2010 |
| WO | WO 2010/032875 | 3/2010 |
| WO | WO 2010/038081 | 4/2010 |
| WO | WO 2010/051223 | 5/2010 |
| WO | WO 2010/080864 | 7/2010 |
| WO | WO 2010/090875 | 8/2010 |
| WO | WO 2010/097248 | 9/2010 |
| WO | WO 2010/129802 | 11/2010 |
| WO | WO 2010/134533 | 11/2010 |
| WO | WO 2010/144468 | 12/2010 |
| WO | WO 2001/000213 | 1/2011 |
| WO | WO 2011/016472 | 2/2011 |
| WO | WO 2011/065800 | 6/2011 |
| WO | WO 2011/090760 | 7/2011 |
| WO | WO 2012/012619 | 1/2012 |
| WO | WO 2012/044936 | 4/2012 |
| WO | WO 2012/045010 | 4/2012 |
| WO | WO 2012/045020 | 4/2012 |
| WO | WO 2012/145569 | 10/2012 |

OTHER PUBLICATIONS

Sakurai ("Practical resolution of 3-aminopyrrolidine via diastereomeric salt formation with (S)-2-methoxy-2-phenylacetic acid" Tetrahedron: Asymmetry, 19, 2008, p. 1622-1625) (Year: 2008).*
Friedfeld ("Bis(phosphine)cobalt Dialkyl Complexes for Directed Catalytic Alkene Hydrogenation" J. Am. Chem. Soc., 2014, vol. 136, p. 13178-13181, including SI p. S1-S21) (Year: 2014).*
Adeyeye, M. C. et al. (Eds.), *Preformulation in Solid Dosage Form Development*, CRC Press, 2008, pp. 239-240.
Alcorn et al., "c-Jun N-Terminal Kinase 1 Is Required for the Development of Pulmonary Fibrosis," Am. J. Respir. Cell. Mol. Biol. 40:422-432 (2009).
Bogoyevitch et al., "c-Jun N-terminal kinase (JNK) signaling: Recent advances and challenges," Biochimica et Biophysica Acta 1804:463-475 (2010).
Bosseray et al., PubMed Abstract (Pathol. Biol. (Paris) 50(8):483-492), Oct. 2002.
Bundgaard, "Design of prodrugs: Bioreversible derivatives for various functional groups and chemical entities," Design of Prodrugs, Chapter 1, p. 1, 1985.
Cohen P., "Protein kinases—the major drug targets of the twenty-first century?" Nat. Rev. Drug Discov. 1(4):309-315 (2002).

(56) References Cited

OTHER PUBLICATIONS

Cohen P., "The role of protein phosphorylation in human health and disease." The Sir Hans Krebs Medal Lecture. Eur. J. Biochem. 268(19):5001-5010 (2001).
Cohen P., "Protein Kinase Inhibitors for the Treatment of Disease: The Promise and the Problems," *Handbook of Experimental Pharmacology*, Springer Berlin Heidelberg, 167 (2005).
Das et al., "Activation of raf-1, MEK, and MAP kinase in prolactin responsive mammary cells," Breast Cancer Res. Treat. 40(2):141-149 (1996).
Davis RJ., "MAPKs: new JNK expands the group," Trends Biochem. Sci. 19(11):470-473 (1994).
Davis RJ., "Signal Transduction by the JNK Group of MAP Kinases," Cell 103:239-252 (2000).
Douglas, Jr., 1996, "Introduction to Viral Diseases," Cecil Textbook of Medicine, 20th Edition, vol. 2, pp. 1739-1747.
Eferl et al., "Development of pulmonary fibrosis through a pathway involving the transcription factor Fra-2/AP-1," PNAS 105(30):10525-10530 (2008).
Fanger et al., "MEKKs, GCKs, MLKs, PAKs, TAKs, and tpls: upstream regulators of the c-Jun amino-terminal kinases?" Curr. Opin. Genet. Dev. 7(1):67-74 (1997).
Gaestel et al., "Protein kinases as small molecule inhibitor targets in inflammation," Curr. Med. Chem. 14(21):2214-2234 (2007).
Goff, PubMed Abstract (J. Gene Med. 3(6):517-528), Nov.-Dec. 2001.
Grimminger et al., "Targeting non-malignant disorders with tyrosine kinase inhibitors," Nat. Rev. Drug Sisc. 9(12):956-970 (2010).
Gupta et al., "Selective interaction of JNK protein kinase isoforms with transcription factors," EMBO J. 15(11):2760-2770 (1996).
Hirabayashi et al., "A novel Syk family kinase inhibitor: design, synthesis, and structure-activity relationship of 1,2,4-triazolo[4,3-c]pyrimidine and 1,2,4-triazolo[1,5-c]pyrimidine derivatives," Bioorg. Med. Chem. 16:7347-7357 (2008).
Hirosumi et al., "A central role for JNK in obesity and insulin resistance," Nature 420:333-336 (2002).
Hisamichi et al., "Synthetic studies on novel Syk inhibitors. Part 1: Synthesis and structure-activity relationships of pyrimidine-5-carboxamide derivatives," Bioorg. Med. Chem. 13:4936-4951 (2005).
Hisamichi et al., "Corrigendum to Synthetic studies on novel Syk inhibitors. Part 1: Synthesis and structure-activity relationships of pyrimidine-5-carboxamide derivatives," Bioorg. Med. Chem. 13:6277-6279 (2005).
Hu et al., "Prolonged activation of the mitogen-activated protein kinase pathway is required for macrophage-like differentiation of a human myeloid leukemic cell line," Cell Growth Differ. 11(4):191-200 (2000).
Hulikal, "L15 Deuterium Labeled Compounds in Drug Discovery Process," Abstract, 2010.
Ichijo H., "From receptors to stress-activated MAP kinases," Oncogene 18(45):6087-6093 (1999).
Ishida et al., "Novel and orally active 5-(1,3,4-oxadiazol-2-yl)pyrimidine derivatives as selective FLT3 inhibitors," Bioorg. Med. Chem. Lett. 18(20):5472-5477 (2008).
Jones et al., "Phase 1 Results From a Study of Romidepsin in Combination With Gemcitabine in Patients With Advanced Solid Tumors," Cancer Invest. 30(6):481-486 (2012).
Kaneto et al., "Oxidative stress and the JNK pathway are involved in the development of type 1 and type 2 diabetes," Curr. Mol. Med. 7:674-686 (2007).
Katayama et al., "Identification of a key element for hydrogen-bonding patterns between protein kinases and their inhibitors," Proteins 73:795-801 (2008).
Kluwe et al., "Modulation of hepatic fibrosis by c-Jun-N-terminal kinase inhibition," Gastroenterology 138:347-359 (2010).
Kodama et al., "c-Jun N-terminal kinase-1 from hematopoietic cells mediates progression from hepatic steatosis to steatohepatitis and fibrosis in mice," Gastroenterology 137:1467-1477.e5 (2009).
Kyriakis JM., "MAP kinases and the regulation of nuclear receptors," Sci. STKE. (48):pe1 (2000).

Lee et al., "Bleomycin induces alveolar epithelial cell death through JNK-dependent activation of the mitochondria death pathway," Am. J. Physiol. Lung Cell. Mol. Physiol. 289(4): L521-L528 (2005).
Le Jeune et al., "Evaluation of imatinib mesylate effects on glioblastoma aggressiveness with SPECT radiotracer 99mTc-(v)-DMSA," Eur. J. Cancer 42(8):1004-1013 (2006).
Liddle et al., "Discovery of GSK143, a highly potent, selective and orally efficacious spleen tyrosine kinase inhibitor," Bioorg. Med. Chem. Lett. 21(20):6188-6194 (2011).
Lin et al., "Connective tissue growth factor induces collagen I expression in human lung fibroblasts through the Rac1/MLK3/JNK/AP-1 pathway," Biochim. Biophys. Acta 1833(12):2823-2833 (2013).
Malhi et al., "Free fatty acids induce JNK-dependent hepatocyte lipoapoptosis," J. Biol. Chem. 281:12093-12101 (2006).
Malhi et al., "Molecular mechanisms of lipotoxicity in nonalcoholic fatty liver disease," Semin Liver Dis. 28(4):360-369 (2008).
Martin et al., "Structure-based design of novel 2-amino-6-phenyl-pyrimido[5',4':5,6]pyrimido[1,2-a]benzimidazol-5(6H)-ones as potent and orally active inhibitors of lymphocyte specific kinase (Lck): synthesis, SAR, and in vivo anti-inflammatory activity," J. Med. Chem. 51(6):1637-1648 (2008).
Nagashima et al., "Synthesis and evaluation of 2-{[2-(4-hydroxyphenyl)-ethyl]amino}pyrimidine-5-carboxamide derivatives as novel STAT6 inhibitors," Bioorg. Med. Chem. 15:1044-1055 (2007).
Nagashima et al., "Identification of 4-benzylamino-2-[(4-morpholin-4-ylphenyl)aminolpyrimidine-5-carboxamide derivatives as potent and orally bioavailable STAT6 inhibitors," Biorg. Med. Chem. 16:6509-6521 (2008).
Nagashima et al., "Novel 7H-pyrrolo[2,3-d]pyrimidine derivatives as potent and orally active STAT6 inhibitors," Bioorg. Med. Chem. 17:6926-6936 (2009).
Ohga et al., "YM-341619 suppresses the differentiation of spleen T cells into Th2 cells in vitro, eosinophilia, and airway hyperresponsiveness in rat allergic models," Eur. J. Pharmacol. 590:409-416 (2008).
Papp et al., "Steady state kinetics of spleen tyrosine kinase investigated by a real time fluorescence assay," Biochemistry 46:15103-15114 (2007).
Pimlott, PubMed Abstract (Nucl. Med. Commun. 26(3):183-188), 2005.
Razonable et al., PubMed Abstract (Herpes 10(3):60-65), Dec. 2003.
Reilly et al., "PRT-060318, a novel Syk inhibitor, prevents heparin-induced thrombocytopenia and thrombosis in a transgenic mouse model," Blood 117(7):2241-2246 (2011).
Sanam et al., "Discovery of potential ZAP-70 kinase inhibitors: pharmacophore design, database screening and docking studies," Eur. J. Med. Chem. 44:4793-4800 (2009).
Sanchez-Tillo et al., "JNK1 Is required for the induction of Mkp1 expression in macrophages during proliferation and lipopolysaccharide-dependent activation," J. Biol. Chem. 282(17):12566-12573 (2007).
Schramek H., "MAP kinases from intracellular signals to physiology and disease," News Physiol. Sci. 17:62-67 (2002).
Schwabe et al., "Differential requirement for c-Jun NH2-terminal kinase in TNF-α- and Fas-mediated apoptosis in hepatocytes," FASEB J. 18(6):720-722 (2004).
Seger and Krebs, "The MAPK signaling cascade," FASEB J. 9(9):726-735 (1995).
Silverman, 1992, "Prodrugs and Drug Delivery Systems," The Organic Chemistry of Drug Design and Drug action, Chapter 8, pp. 352-400.
Singh et al., "Differential effects of JNK1 and JNK2 inhibition on murine steatohepatitis and insulin resistance," Hepatology 49(1):87-96 (2009).
Singh et al., "Discovery and development of spleen tyrosine kinase (SYK) inhibitors," J. Med. Chem. 55(8):3614-3643 (2012).
Sridhar et al., "Protein kinases as therapeutic targets," Pharm. Res. 17(11):1345-1353 (2000).
Storey, R. A. et al. (Eds.), *Solid State Characterization of Pharmaceuticals*, Wiley-Blackwell, 2011, pp. 473-491, 490.
Tedesco et al., "Synthesis and biological activity of heteroaryl 3-(1,1-dioxo-2H-(1,2,4)-benzothiadizin-3-yl)-4-hydroxy-2(1H)-quinolinone derivatives as hepatitis C virus NS5B polymerase inhibitors," Bioorg. Med. Chem. Lett. 19(15):4354-4358 (2009).

(56) References Cited

OTHER PUBLICATIONS

Uehara et al., "c-Jun N-Terminal Kinase Mediates Hepatic Injury after Rat Liver Transplantation," Transplantation 78(3):324-332 (2004).
Vallerie et al., "The role of JNK proteins in metabolism," Sci. Transl. Med. 2(60):1-7 (2010).
Villaseñor et al., "Structural insights for design of potent spleen tyrosine kinase inhibitors from crystallographic analysis of three inhibitor complexes," Chem. Biol. Drug Des. 73:466-470 (2009).
Virkamaki et al., "Protein-protein interaction in insulin signaling and the molecular mechanisms of insulin resistance," J. Clin. Invest. 103(7):931-943 (1999).
Whitmarsh AJ et al., "Signal transduction by MAP kinases regulation by phosphorylation-dependent switches," Sci. STKE. (1):pe1 (1999).
Xie et al., "Pharmacophore modeling study based on known spleen tyrosine kinase inhibitors together with virtual screening for identifying novel inhibitors," Bioorg. Med. Chem. Lett. 19:1944-1949 (2009).
Yoshida et al., "MAP kinase activation and apoptosis in lung tissues from patients with idiopathic pulmonary fibrosis," J. Pathol. 198:388-396 (2002).

\* cited by examiner

METHODS OF SYNTHESIS OF (1R,2R,5R)-5-AMINO-2-METHYLCYCLOHEXANOL HYDROCHLORIDE AND INTERMEDIATES USEFUL THEREIN

This application is a U.S. national stage application of International Patent Application No. PCT/US2016/043511, filed Jul. 22, 2016, which claims the benefit of priority to U.S. Provisional Application Ser. No. 62/196,363, filed Jul. 24, 2015, which is incorporated herein by reference in its entirety and for all purposes.

FIELD

Provided herein are methods and intermediates for making (1R,2R,5R)-5-amino-2-methylcyclohexanol hydrochloride, which are useful for the preparation of compounds useful for the treatment of a disease, disorder, or condition associated with the JNK pathway.

BACKGROUND

The connection between abnormal protein phosphorylation and the cause or consequence of diseases has been known for over 20 years. Accordingly, protein kinases have become a very important group of drug targets. (See Cohen, *Nature*, 1:309-315 (2002), Gaestel et al. *Curr. Med. Chem.* 14: 2214-223 (2007); Grimminger et al. *Nat. Rev. Drug Disc.* 9(12):956-970 (2010)). Various protein kinase inhibitors have been used clinically in the treatment of a wide variety of diseases, such as cancer and chronic inflammatory diseases, including rheumatoid arthritis and psoriasis. (See Cohen, *Eur. J. Biochem.*, 268:5001-5010 (2001); Protein Kinase Inhibitors for the Treatment of Disease: The Promise and the Problems, *Handbook of Experimental Pharmacology*, Springer Berlin Heidelberg, 167 (2005)).

JNK is a ubiquitously expressed serine/threonine kinase belonging, together with ERK (extracellular-regulated kinase) and p38, to the family of mitogen-activated protein kinases (MAPKs). (Kyriakis J M, *Sci. STKE* (48):pe1 (2000); Whitmarsh A J, et al. *Sci. STKE* (1):pe1 (1999); Schramek H, *News Physiol. Sci.* 17:62-7 (2002); Ichijo H, *Oncogene* 18(45):6087-93 (1999)). MAPKs are important mediators of signal transduction from the cell surface to the nucleus, using phosphorylation cascades to generate a coordinated response by a cell to an external stimulus by phosphorylation of selected intracellular proteins, including transcription factors. Additionally, JNK also phosphorylates non-nuclear proteins, for example, IRS-1, and Bcl-2 family members. (Davis R J, *Trends Biochem. Sci.* 9(11):470-473 (1994); Seger R et al., *FASEB J.*; 9(9):726-35 (1995); Fanger G R et al., *Curr. Opin. Genet. Dev.*; 7(1):67-74 (1997)).

The elucidation of the intricacy of protein kinase pathways and the complexity of the relationship and interaction among and between the various protein kinases and kinase pathways highlights the importance of developing pharmaceutical agents capable of acting as protein kinase modulators, regulators or inhibitors that have beneficial activity on multiple kinases or multiple kinase pathways. The compound chemically named 2-(tert-butylamino)-4-((1R,3R,4R)-3-hydroxy-4-methylcyclohexylamino)-pyrimidine-5-carboxamide (alternatively named 2-[(1,1-dimethylethyl)amino]-4-[[(1R,3R,4R)-3-hydroxy-4-methylcyclohexyl]amino]-5-pyrimidinecarboxamide; and referred to herein as "Compound I"), an inhibitor of the JNK pathway, is disclosed in U.S. Patent Application Publication No. 2013/0029987, published on Jan. 31, 2013, International Pub. No. WO 2012/145569 and U.S. patent application Ser. No. 14/608,314, filed Jan. 29, 2015, the entireties of each of which are incorporated by reference herein. Accordingly, there remains a need for new processes for the preparation of Compound I.

Citation or identification of any reference in Section 2 of this application is not to be construed as an admission that the reference is prior art to the present application.

SUMMARY

Provided herein are processes and intermediates useful for the preparation of Compound I:

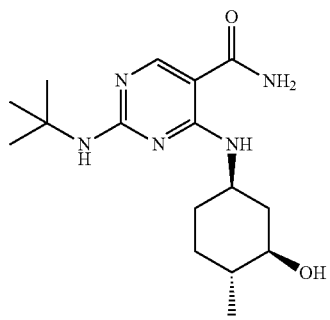

having the name 2-(tert-butylamino)-4-((1R,3R,4R)-3-hydroxy-4-methylcyclohexylamino)-pyrimidine-5-carboxamide, which is useful for the treatment of a disease, disorder, or condition associated with the JNK pathway.

In particular, provided herein are processes for making a compound of formula (A):

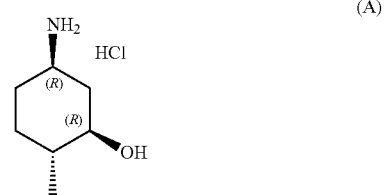

having the name (1R,2R,5R)-5-amino-2-methylcyclohexanol hydrochloride.

Provided is a method for preparing a compound of formula (A),

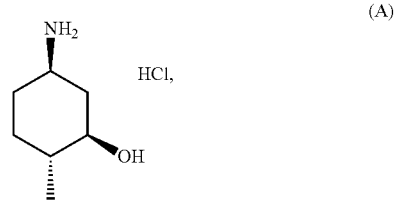

comprises the steps of:

(a) contacting a compound of formula (1),

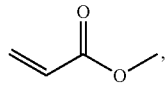
(1)

with a compound of formula (2),

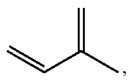
(2)

in the presence of a Lewis Acid in a solvent to provide a compound of formula (3),

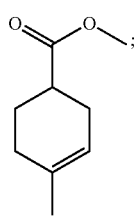
(3)

(b) contacting the compound of formula (3) of step (a) with an aqueous base to provide a compound of formula (4),

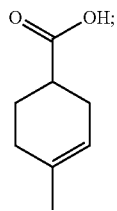
(4)

(c) contacting the compound of formula (4) of step (b) with DMF and a chlorinating agent in an organic solvent, followed by treatment of the resulting acid chloride derivative with aqueous ammonia to provide a compound of formula (5),

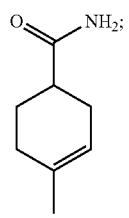
(5)

(d) contacting the compound of formula (5) of step (c) with an aqueous solution of NaOH and NaOCl to provide a compound of formula (6),

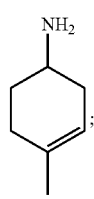
(6)

(e) contacting the compound of formula (6) of step (d) with (+)-dibenzoyl-D-tartaric acid monohydrate in a solvent to provide a compound of formula (7),

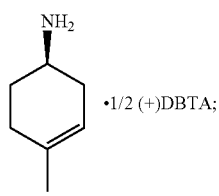
(7)

(f) contacting the compound of formula (7) of step (e) with an aqueous base, followed by treatment of the resulting free base with Boc$_2$O in an organic solvent to provide a compound of formula (8),

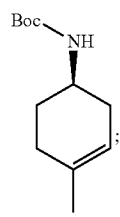
(8)

(g) contacting the compound of formula (8) of step (f) with a mixture of a reducing agent, a chiral auxiliary and a Lewis acid in a solvent, followed by treatment with an oxidant in the presence of a base to provide a compound of formula (9),

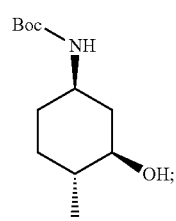
(9)

and (h) contacting the compound of formula (9) of step (g) with a solution of hydrochloric acid in a solvent to provide the compound of formula (A). In one embodiment, the Lewis acid of step (a) is AlCl$_3$. In a further embodiment, the solvent of step (a) is DCM. In one embodiment, the base of step (b) is NaOH. In one embodiment, the chlorinating agent of step (c) is SOCl$_2$. In a further embodiment, the organic solvent of step (c) is DCM. In one embodiment, the solvent of step (e) is MeOH. In one embodiment, the base of step (f) is NaOH. In a further embodiment, the organic solvent of step (f) is DCM. In one embodiment, the reducing agent of step (g) is NaBH$_4$. In a further embodiment, the chiral auxiliary of step (g) is α-pinene. In a particular embodiments, the Lewis acid of step (g) is BF$_3$.Et$_2$O. In another particular embodiment, the solvent of step (g) is THF. In still another embodiment, the oxidant of step (g) is H$_2$O$_2$. In a specific embodiment, the base of step (g) is NaOH. In one embodiment, the solvent of step (h) is IPA.

In certain aspects, Compound I is useful for inhibiting a kinase in a cell expressing said kinase, for example JNK1 or JNK2. In other aspects, Compound I is useful for treating or preventing a condition treatable or preventable by inhibition of a JNK pathway, as described herein. In another aspect, Compound I is useful for treating or preventing one or more disorders selected from interstitial pulmonary fibrosis, systemic sclerosis, scleroderma, chronic allograft nephropathy, antibody mediated rejection, or lupus. In yet another aspect, Compound I is useful for treating or preventing liver fibrotic disorders, or diabetes and/or metabolic syndrome leading to liver fibrotic disorders, as described herein.

The present embodiments can be understood more fully by reference to the detailed description and examples, which are intended to exemplify non-limiting embodiments.

DETAILED DESCRIPTION

Definitions

Figure 1:
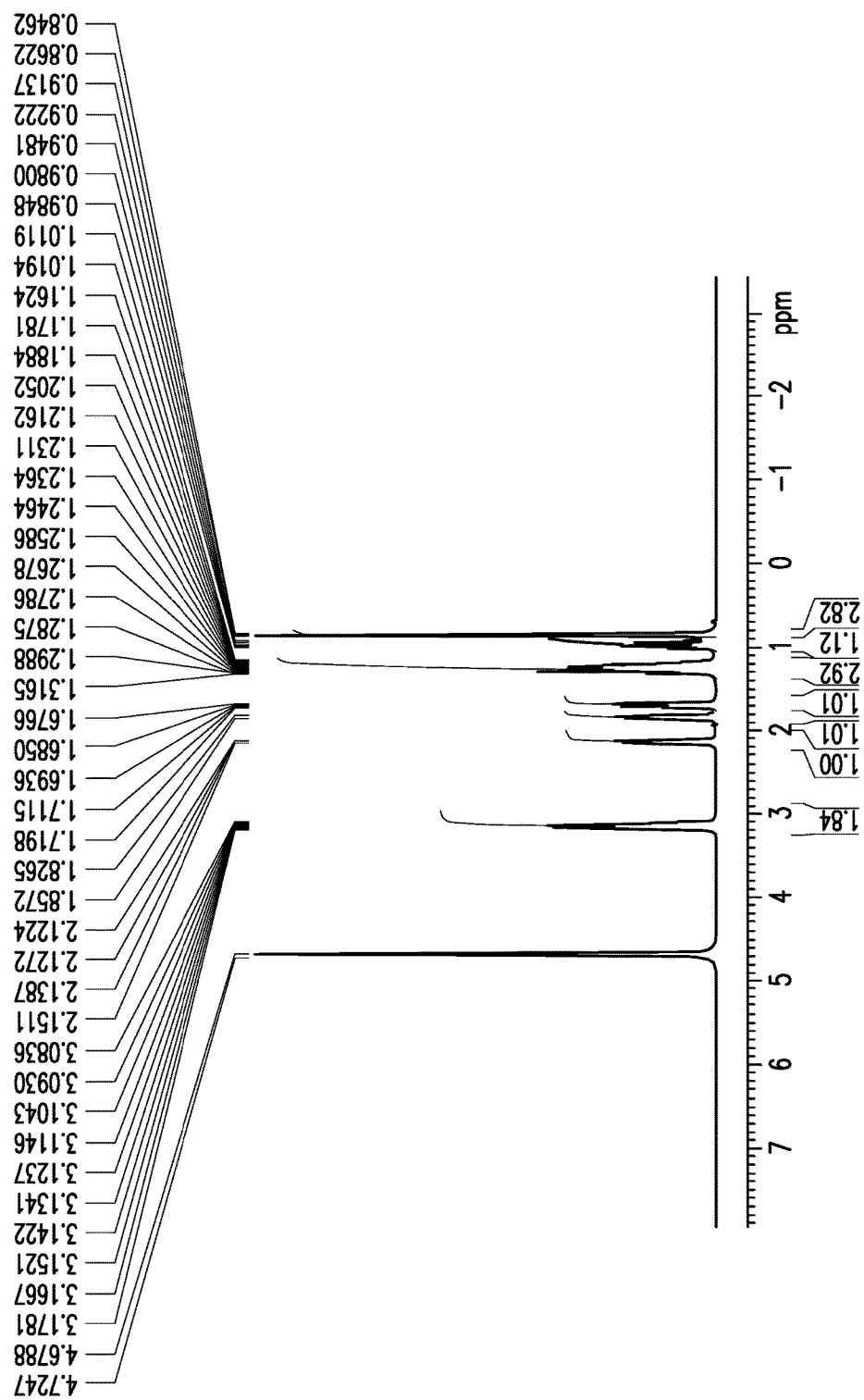
FIG. 1 depicts a $^1$H NMR spectrum of Compound (A) in D$_2$O.
Figure 2:
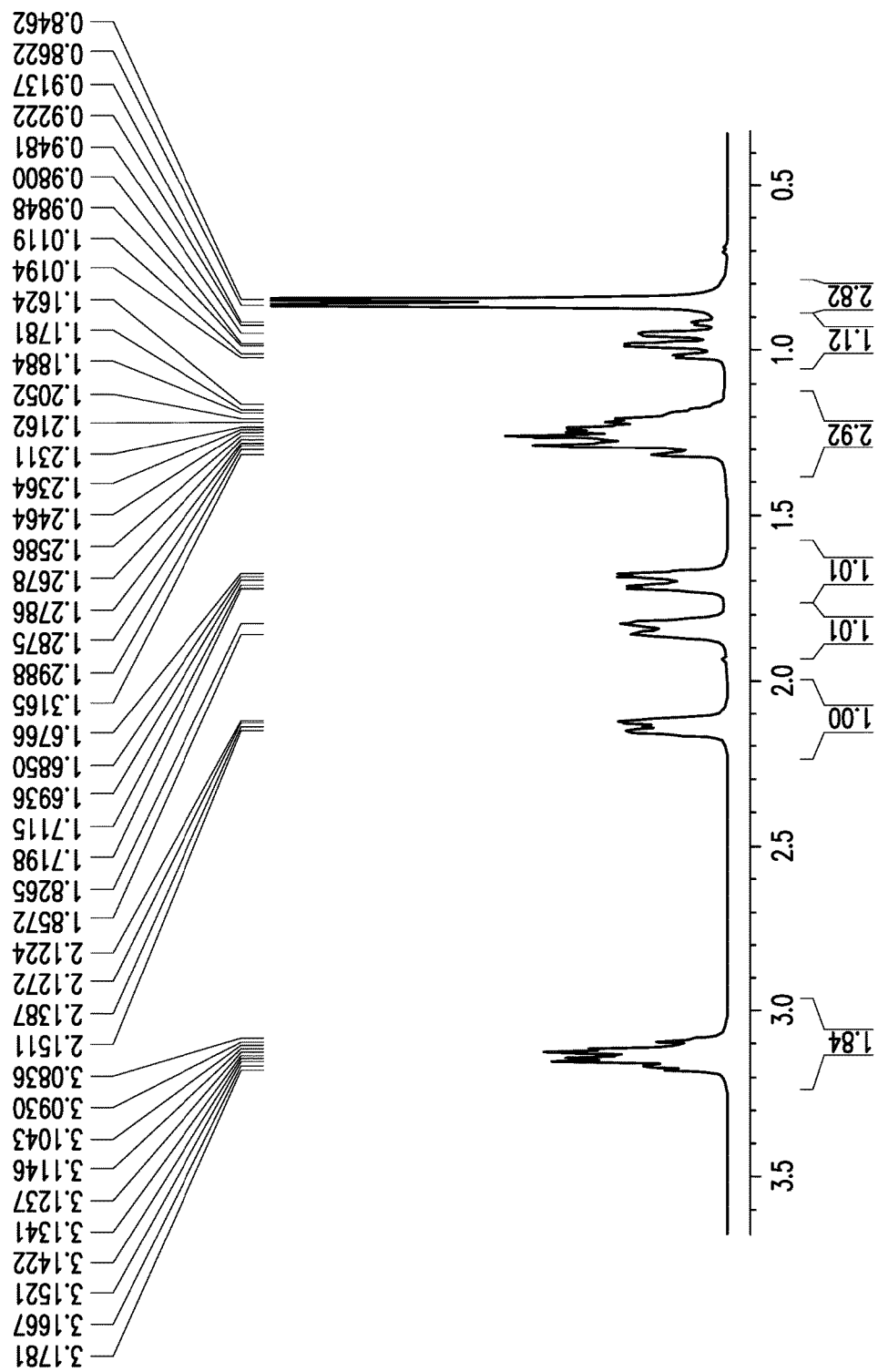
FIG. 2 depicts an expanded (~0.2-3.6 ppm) $^1$H NMR spectrum of Compound (A) in D$_2$O.
Figure 3:
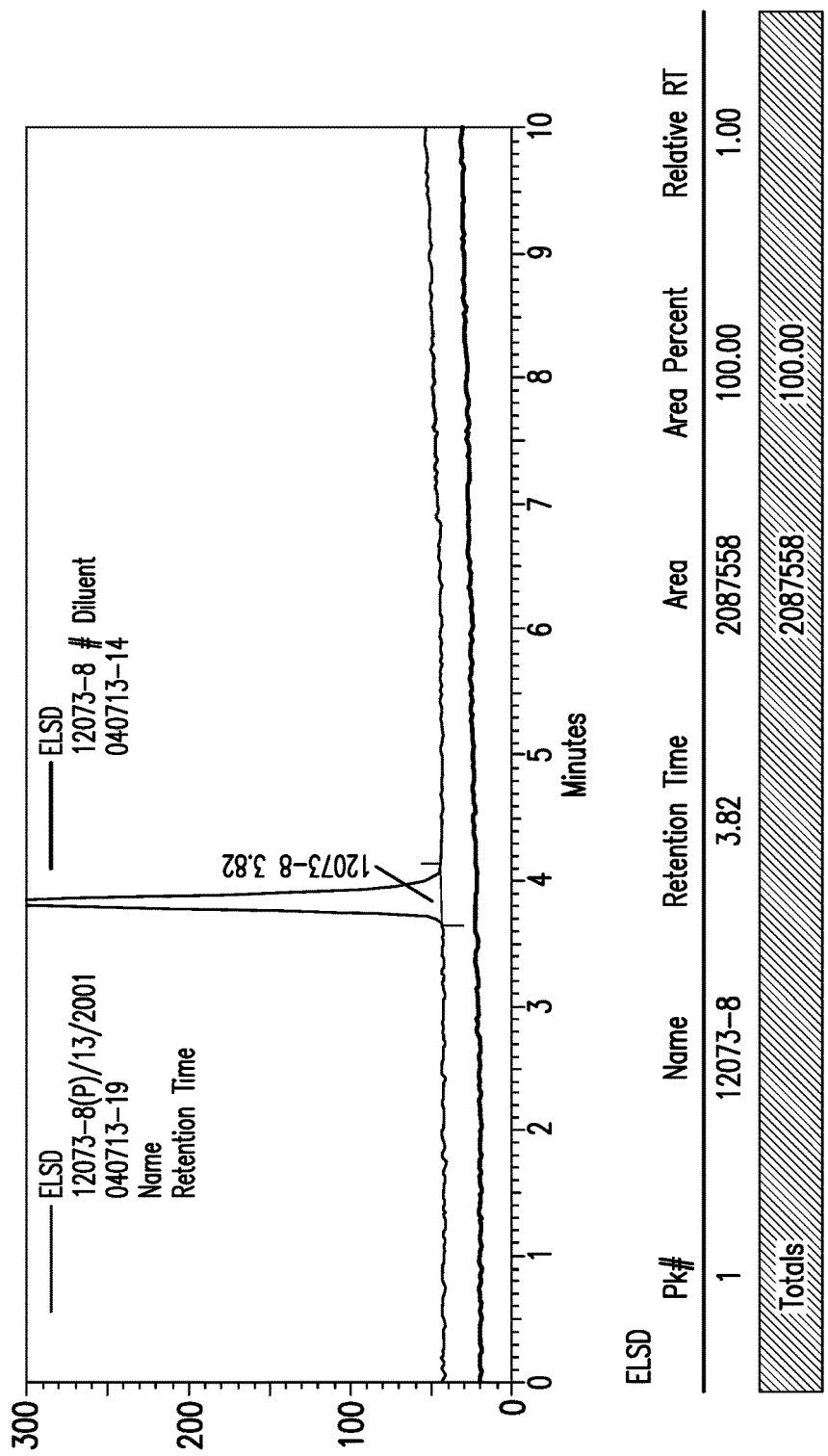
FIG. 3 depicts a HPLC chromatogram of Compound (A).
Figure 4:
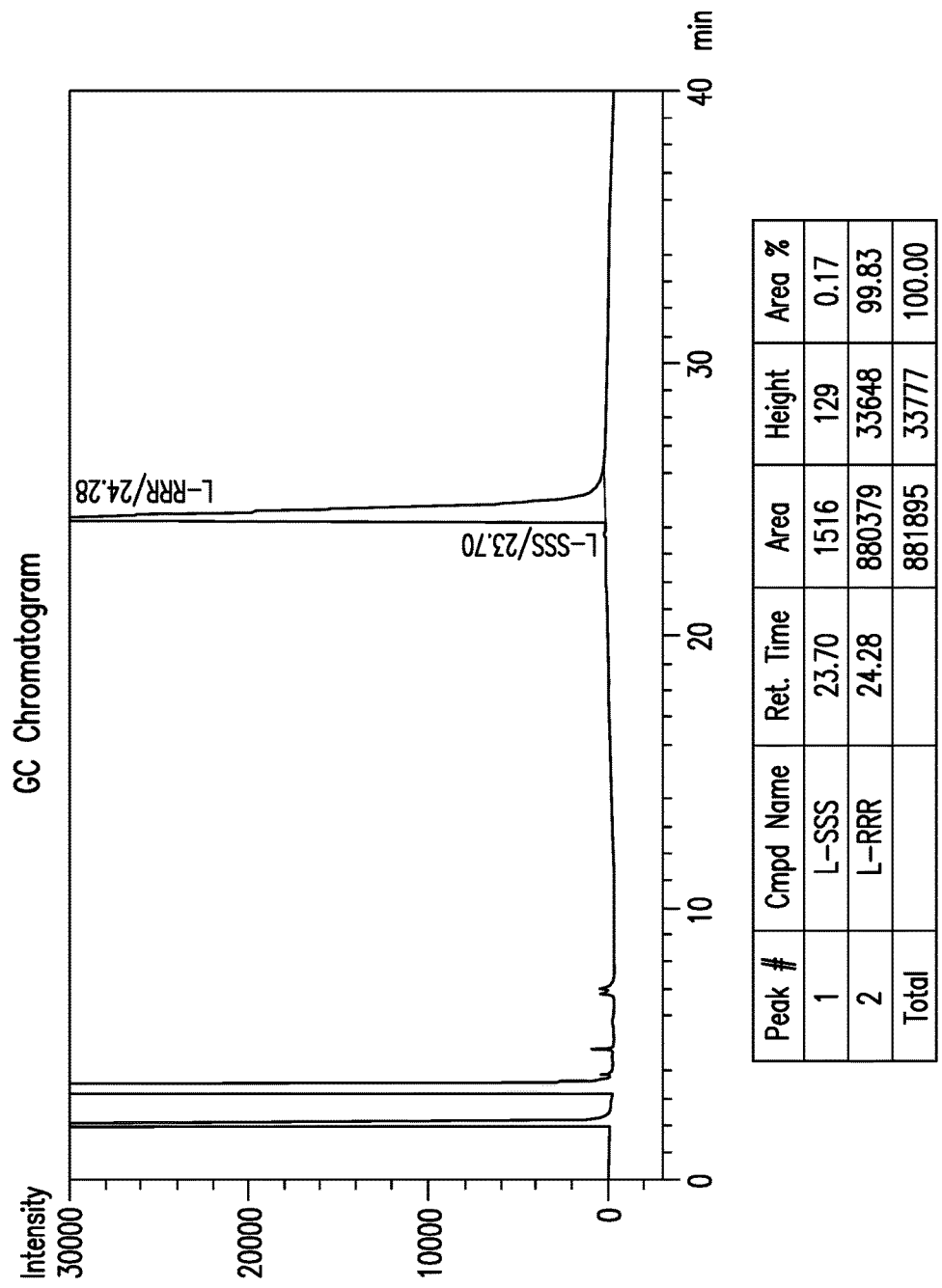
FIG. 4 depicts a chiral GC chromatogram of Compound (A).

As used herein, and in the specification and the accompanying claims, the indefinite articles "a" and "an" and the definite article "the" include plural as well as single referents, unless the context clearly indicates otherwise.

As used herein, and unless otherwise specified, the terms "about" and "approximately," when used in connection with amounts or weight percents of ingredients of a process, mean an amount or weight percent that is recognized by one of ordinary skill in the art to provide an effect equivalent to that obtained from the specified amount, or weight percent. In certain embodiments, the terms "about" and "approximately," when used in this context, contemplate an amount or weight percent within 30%, within 20%, within 15%, within 10%, or within 5%, of the specified amount or weight percent.

"JNK" means a protein or an isoform thereof expressed by a JNK1, JNK2, or JNK3 gene (Gupta, S., Barrett, T., Whitmarsh, A. J., Cavanagh, J., Sluss, H. K., Derijard, B. and Davis, R. J. *The EMBO J.* 15:2760-2770 (1996)).

"Treating" as used herein, means an alleviation, in whole or in part, of a disorder, disease or condition, or one or more of the symptoms associated with a disorder, disease, or condition, or slowing or halting of further progression or worsening of those symptoms, or alleviating or eradicating the cause(s) of the disorder, disease, or condition itself. In one embodiment, the disorder is a condition treatable or preventable by inhibition of a JNK pathway, as described herein. In another embodiment, the disorder is selected from interstitial pulmonary fibrosis, systemic sclerosis, scleroderma, chronic allograft nephropathy, antibody mediated rejection, or lupus. In yet another embodiment, the disorder is a liver fibrotic disorder, or diabetes and/or metabolic syndrome leading to liver fibrotic disorders, as described herein. In some embodiments, the disorder is a liver fibrotic disorder, such as non-alcoholic steatohepatitis, steatosis (i.e. fatty liver), cirrhosis, primary sclerosing cholangitis, primary biliary cirrhosis, hepatitis, hepatocellular carcinoma, or liver fibrosis coincident with chronic or repeated alcohol ingestion (alcoholic hepatitis), with infection (e.g., viral infection such as HCV), with liver transplant, or with drug induced liver injury (e.g., acetaminophen toxicity). In some embodiments, "treating" means an alleviation, in whole or in part, of a disorder, disease or condition, or symptoms associated with diabetes or metabolic syndrome leading to liver fibrotic disorders, such as non-alcoholic steatohepatitis, steatosis (i.e. fatty liver), hepatitis or cirrhosis, or a slowing, or halting of further progression or worsening of those symptoms. In one embodiment, the symptom is jaundice.

"Preventing" as used herein, means a method of delaying and/or precluding the onset, recurrence or spread, in whole or in part, of a disorder, disease or condition; barring a subject from acquiring a disorder, disease, or condition; or reducing a subject's risk of acquiring a disorder, disease, or condition. In one embodiment, the disorder is a condition treatable or preventable by inhibition of a JNK pathway, as described herein. In another embodiment, the disorder is selected from interstitial pulmonary fibrosis, systemic sclerosis, scleroderma, chronic allograft nephropathy, antibody mediated rejection, or lupus. In one embodiment, the disorder is a liver fibrotic disorder, or diabetes or metabolic syndrome leading to liver fibrotic disorders, as described herein, or symptoms thereof.

"Patient" or "subject" is defined herein to include animals, such as mammals, including, but not limited to, primates (e.g., humans), cows, sheep, goats, horses, dogs, cats, rabbits, rats, mice, monkeys, chickens, turkeys, quails, or guinea pigs and the like, in one embodiment a mammal, in another embodiment a human. In one embodiment, a subject is a human having or at risk for having interstitial pulmonary fibrosis, systemic sclerosis, scleroderma, chronic allograft nephropathy, antibody mediated rejection, or lupus. In another, a subject is a human having or at risk for having liver fibrotic disorders or diabetes or metabolic syndrome leading to liver fibrotic disorders, or a condition, treatable or preventable by inhibition of a JNK pathway, or a symptom thereof.

Compound (A)

As described in U.S. Patent Application Publication No. 2013/0029987, published on Jan. 31, 2013, International Pub. No. WO 2012/145569 and U.S. patent application Ser. No. 14/608,314, filed Jan. 29, 2015, the entireties of each of which are incorporated by reference herein, compounds of formula I can be prepared as shown in Scheme A.

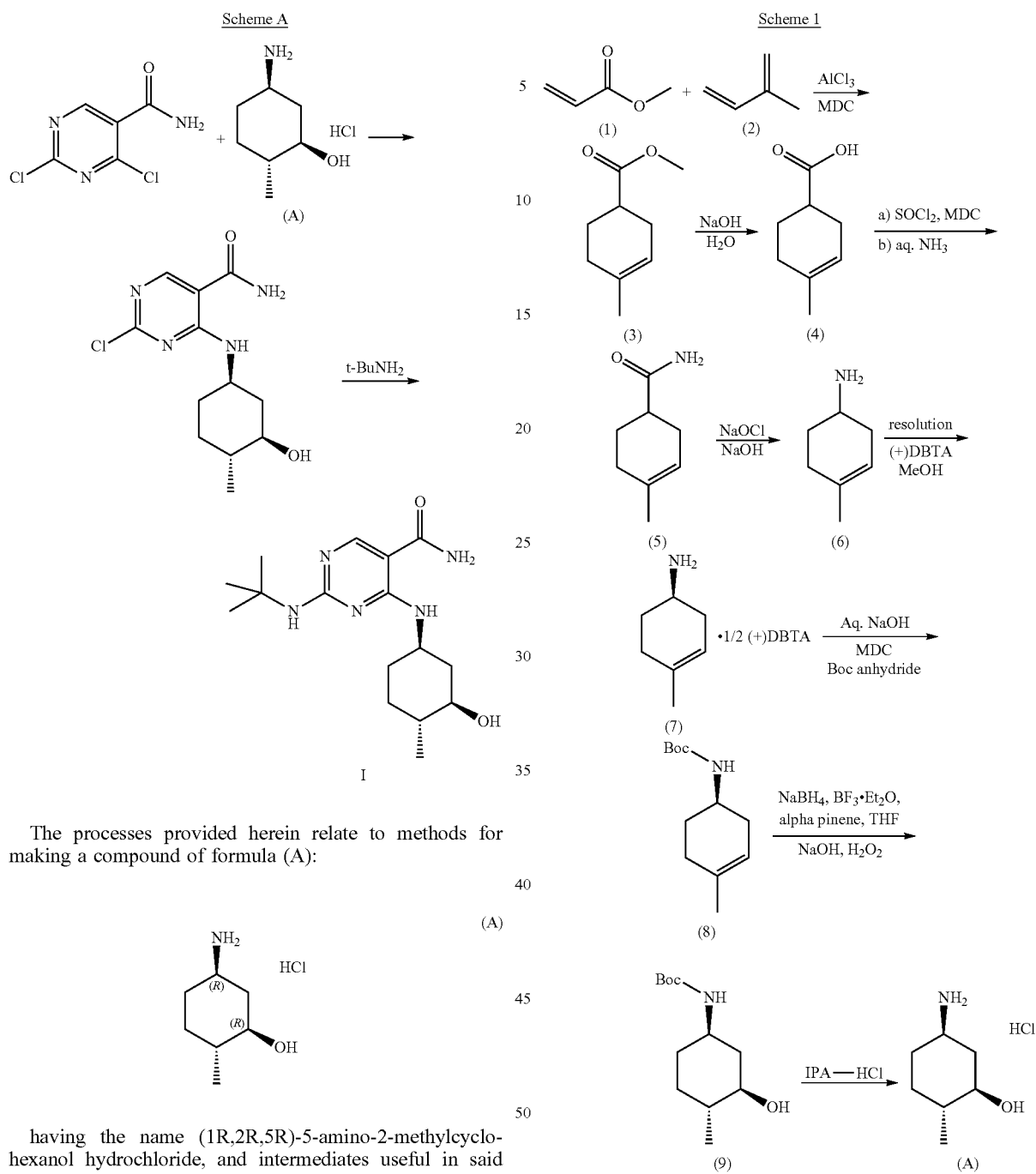

The processes provided herein relate to methods for making a compound of formula (A):

(A)

having the name (1R,2R,5R)-5-amino-2-methylcyclohexanol hydrochloride, and intermediates useful in said processes.

It should be noted that if there is a discrepancy between a depicted structure and a name given to that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

Methods for Making Compound (A)

By way of example and not limitation, the compound of formula (A) can be prepared as outlined in Scheme 1 shown below, as well as in the examples set forth herein.

In one aspect, provided herein are methods for preparing a compound of formula (A):

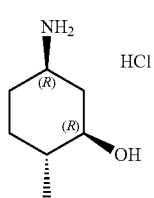

(A)

the methods comprising contacting a compound of formula (9):

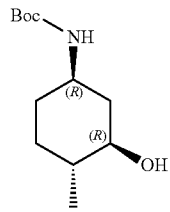

(9)

with hydrochloric acid in a solvent.

In some embodiments, the solvent is methanol, 2-propanol (IPA), ether or dioxane. In one embodiment, the solvent is 2-propanol (IPA).

In some embodiments, the methods further comprise preparing a compound of formula (9):

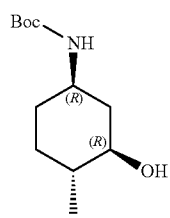

(9)

the methods comprising contacting a compound of formula (8):

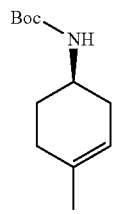

(8)

with a mixture of a reducing agent, a chiral auxiliary and a Lewis acid in a solvent, followed by treatment with an oxidant in the presence of a base.

In one embodiment, the reducing agent is $NaBH_4$. In another embodiment, the chiral auxiliary is α-pinene. In another embodiment, the Lewis acid is $BF_3.Et_2O$. In one embodiment, the solvent is THF or EtOH. In another embodiment, the solvent is THF. In one embodiment, the oxidant is $H_2O_2$ or oxone. In another, the oxidant is $H_2O_2$. In one embodiment, the base is NaOH.

In some embodiments, the methods further comprise preparing a compound of formula (8):

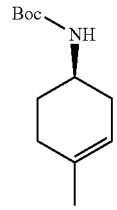

(8)

the methods comprising contacting a compound of formula (7):

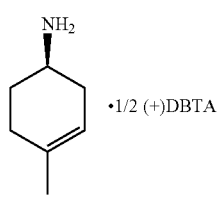

(7)

with an aqueous base, followed by treatment of the resulting free base with $Boc_2O$ in an organic solvent, optionally in the presence of a second base.

In one embodiment, the aqueous base is aqueous NaOH. In one embodiment, the organic solvent is DCM or ether. In another embodiment, the organic solvent is DCM. In one embodiment, the second base is triethylamine.

In some embodiments, the methods further comprise preparing a compound of formula (7):

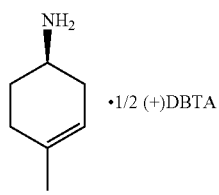

(7)

the methods comprising contacting a compound of formula (6):

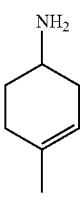

(6)

with (+)-dibenzoyl-D-tartaric acid monohydrate in a solvent.

In one embodiment, the solvent is methanol.

In some embodiments, the methods further comprise preparing a compound of formula (6):

the methods comprising contacting a compound of formula (5):

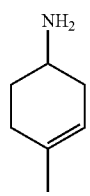
(6)

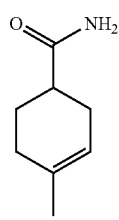
(5)

with an aqueous solution of NaOH and NaOCl.

In some embodiments, the methods further comprise preparing a compound of formula (5):

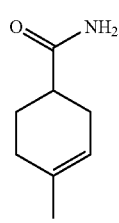
(5)

the methods comprising contacting a compound of formula (4):

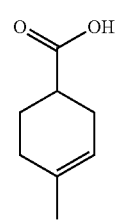
(4)

with DMF and a chlorinating agent in an organic solvent, followed by treatment of the resulting acid chloride derivative with aqueous ammonia.

In one embodiment, the chlorinating agent is oxalayl chloride or SOCl₂. In one embodiment, the chlorinating agent is SOCl₂. In one embodiment, the organic solvent is DCM.

In some embodiments, the methods further comprise preparing a compound of formula (4):

the methods comprising contacting a compound of formula (3):

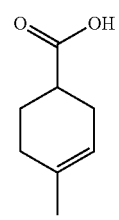
(4)

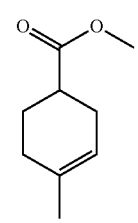
(3)

with an aqueous base.

In one embodiment, the base is LiOH or NaOH. In another embodiment, the base is NaOH.

In some embodiments, the methods further comprise preparing a compound of formula (3):

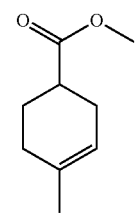
(3)

the methods comprising contacting a compound of formula (1):

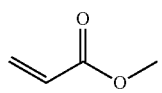
(1)

with a compound of formula (2):

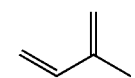
(2)

in a solvent, in the presence of a Lewis acid.

In one embodiment, the Lewis acid is AlCl₃. In one embodiment, the solvent is DCM.

Intermediates useful in the processes provided herein include:

13

(1) 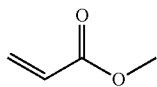

(2) 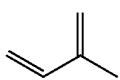

(3) 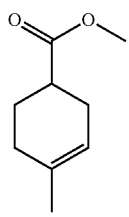

(4) 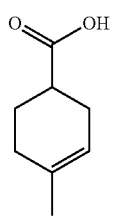

(5) 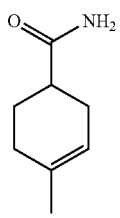

(6) 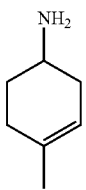

(7) 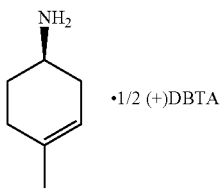

(8) 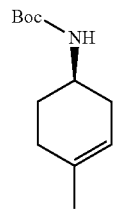

14

-continued (9) 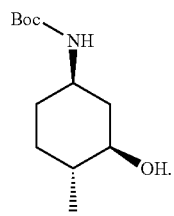

Utility of Compound I

Compound I has utility as a pharmaceutical to treat, prevent or improve conditions in animals or humans. In particular, Compound I is active against protein kinases, particularly JNK1 and/or JNK2. Uses of Compound I are disclosed in U. S. Patent Publication No. 2013/0029987, published Jan. 31, 2013, which is incorporated by reference herein in its entirety.

Abbreviations

The following abbreviations are used in descriptions and examples:
ACN: Acetonitrile
Boc: tert-Butoxycarbonyl
n-BuOH: n-Butanol
DBTA: Dibenzoyl-D-tartaric acid
DBU: 1,8-Diazabicyclo[5.4.0]undec-7-ene
DCM: Dichloromethane
DIPEA: N,N-Diisopropylethylamine
DMAc: N,N-Dimethylacetamide
DMF: N,N-Dimethylformide
DMSO: Dimethylsulfoxide
EtOAc: Ethyl acetate
EtOH: Ethanol
GC: Gas Chromatography
IPA: 2-Propanol
IPAc: Isopropyl acetate
LC: Liquid Chromatography
MeOH: Methanol
2-MeTHF: 2-Methyl tetrahydrofuran
MS: Mass spectrometry
MTBE: tert-Butyl methyl ether
NMP: N-Methyl-2-pyrrolidone
NMR: Nuclear magnetic resonance
OR: Optical Rotation
SFC: Supercritical Fluid Chromatography
Tf: Triflate or trifluoromethanesulfonyl
TFE: 2,2,2-Trifluoroethanol
THF: Tetrahydrofuran

SYNTHETIC EXAMPLES

The following synthetic examples, presented by way of illustration and not limitation, show methods for the preparation of Compound (A). ACD/NAME (Advanced Chemistry Development, Inc., Ontario, Canada) was used to generate names for chemical structures and Chemdraw (Cambridgesoft, Perkin Elmer, Waltham, Mass.) to draw the chemical structures. In certain cases, Chemdraw was used to generate names for chemical structures.

Example 1: Synthesis of (1R,2R,5R)-5-amino-2-methylcyclohexanol hydrochloride

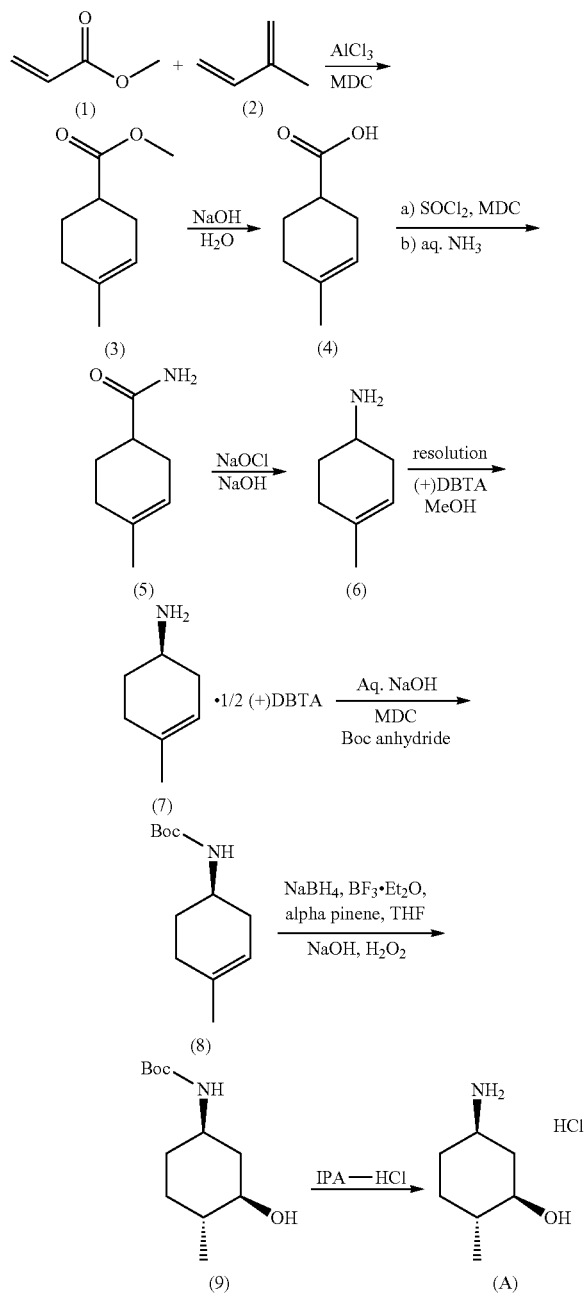

Methyl 4-methylcyclohex-3-enecarboxylate (3)

To a reactor was added DCM (2.5 L) and methyl acrylate (1) (500.0 g) at 20-25° C. under an atmosphere of nitrogen. After stirring for 5 min., the batch was cooled to 0° C., and isoprene (2) (593.4 g) was added over 5-10 min. After stirring for 5 min. at 25° C., anhydrous $AlCl_3$ (116.2 g) was added over 60-90 min. while maintaining the temperature between 0-10° C. After stirring at 0-10° C. for 30 min., the batch was gradually warmed to 25° C. and stirred (≥3 h) at that temperature until HPLC indicated <1% unreacted methyl acrylate (1). Upon completion of the reaction, as indicated by HPLC, the batch was cooled to 0° C. and quenched with HCl solution (250 mL conc. HCl and 1750 mL water) over a period of 30-60 min. while keeping the temperature below 10° C. during the quenching period. The batch was allowed to warm upto 25° C., and was filtered through Hyflo to remove the undissolved solid while rinsing the residue with DCM (500 mL). The filtrate was extracted with DCM (1 L), and the combined organic layers were successively washed with 5% aqueous $NaHCO_3$ (1 L) solution and brine (1 L). DCM was distilled out from the organic fraction at 40-50° C. under atmospheric condition to furnish crude methyl 4-methylcyclohex-3-enecarboxylate (3) as a brown liquid (~1200 g, quantitative yield, 85.54% purity by HPLC), which was used for the next step without purification.

4-Methylcyclohex-3-enecarboxylic acid (4)

To a solution of NaOH (290.4 g NaOH in 1800 mL water) in a reactor at 15-20° C. was slowly added 4-methylcyclohex-3-enecarboxylate (3) (1200 g crude material from above; 895.63 g considering 100% yield), while keeping the temperature below 25° C. The batch was gradually warmed to 35-40° C. and the resulting clear solution was stirred (≥2 h) at that temperature until HPLC indicated <1% unreacted intermediate (3). Upon completion of the reaction, as indicated by HPLC, the batch was brought to 25° C. and quenched with water (900 mL). The aqueous mixture containing the product was washed with DCM (2×900 mL). The aqueous layer was cooled to 0-10° C. and acidified with conc. HCl (630 mL) to pH 1-2 while keeping the temperature below 20° C. After stirring the mixture for 10 min. at 20-25° C., the product was extracted from the aqueous layer with DCM (2×900 mL). The combined organic layers were washed with water (900 mL). DCM was distilled out from the organic fraction at 40-45° C. and the resulting solid mass was vacuum dried for 1 h at 40-45° C. to furnish, upon cooling to room temperature, 4-methylcyclohex-3-enecarboxylic acid (4) (707.51 g, 86.90% yield based on HPLC, 85.28% purity by HPLC). The product thus obtained was dissolved in DCM (750 mL) and used for the next step without purification.

4-Methylcyclohex-3-enecarboxamide (5)

To a reactor containing a solution of 4-methylcyclohex-3-enecarboxylic acid (4) in DCM from above (~1614 g, containing ~690 g of intermediate (4)) was added DMF (6.9 mL) at 25° C. under an atmosphere of nitrogen. After stirring the reaction for 5 min., thionyl chloride (673.44 g) was added over a period of 30-60 min. while keeping the temperature below 20° C. After stirring for 10 min. at 15-20° C., the reaction was warmed to 25-30° C. and stirred (≥2 h) at that temperature until TLC indicated <2% unreacted intermediate (4). Upon completion of the reaction, as indicated by TLC, the solvents were completely distilled out under vacuum. The resulting mixture was vacuum dried for 30 min. at 35-40° C. and then brought to room temperature. The mass thus obtained was slowly added over a period of 30-60 min. to an ice-cold solution (0-5° C.) of aqueous ammonia (2.76 L) in a separate reactor while keeping the temperature below 10° C. After stirring the reaction mixture for 30 min. at 0-10° C., the resulting residue was filtered off, washed with water, and vacuum dried over air. The product was further dried in an air oven at 45-50° C. and brought to room temperature to furnish 4-methylcyclohex-3-enecarboxamide (5) as an off-white solid (604 g, 88.15% yield based on HPLC, 86.55% purity by HPLC), which was used for the next step without purification.

4-Methylcyclohex-3-enamine (6)

To a solution of NaOH (481.68 g) and water (2.16 L) in a reactor at −5° C. to 5° C. was added slowly a solution of 10.5% w/w sodium hypochlorite (4587.4 g) under an atmosphere of nitrogen. After stirring for 10 min., 4-methylcyclohex-3-enecarboxamide (5) (600 g) was gradually added in portions at −5° C. to 5° C. The reaction was stirred for 6 h at a temperature below 10° C., gradually warmed to 25° C. and stirred (≥5 h) at that temperature until HPLC indicated <5% unreacted intermediate (5). Upon completion of the reaction, as indicated by HPLC, toluene (1.2 L) was added. The mixture was cooled to 0-5° C. and acidified with conc. HCl (1.5 L) to pH 1-1.5 while keeping the temperature below 20° C. After stirring for 5 min., the organic layer was separated, and the aqueous layer was washed with toluene (1.2 L). The aqueous layer was then cooled to 0-5° C., and basified with aqueous NaOH solution (2.0 kg NaOH and 1340 mL $H_2O$) to pH>13 while keeping the temperature below 20° C. The product was extracted with DCM (2×1.5 L), and the combined organic layers were dried over sodium sulfate and filtered. DCM was distilled out from the filtrate at 40-60° C. under atmospheric conditions. The resulting residue was cooled to room temperature to furnish 4-methylcyclohex-3-enamine (6) (377.4 g, 78.74% yield based on HPLC, 85.74% purity by HPLC), which was used for the next step without purification.

(R)-4-Methylcyclohex-3-enamine hemi-dibenzoyl-D(+)-tartarate (7)

A solution of (+)-dibenzoyl-D-tartaric acid monohydrate (1015.3 g) in methanol (3 L) was gradually brought to reflux. To this refluxing solution was slowly added a solution of 4-methylcyclohex-3-enamine (6) (300 g) in methanol (300 mL) over a period of 60-75 min. The reaction mixture was refluxed for 2 h and then gradually cooled to 25° C. over 4-5 h. After stirring the reaction mixture for an additional 1 h at 25° C., the resulting residue was filtered, washed with methanol, and dried under vacuum for 30 min. Chiral HPLC of the Boc protected product (prepared by converting an aliquot to the Boc derivative) indicated 71.22% of the desired (R)-4-methylcyclohex-3-enamine hemi-dibenzoyl-D(+)-tartarate (7), and 28.72% of the corresponding S-isomer.

The crude product obtained above (~645 g) was treated with (+)-dibenzoyl-D-tartaric acid monohydrate (123.1 g) and methanol (3.8 L), and the resulting mixture was refluxed for 2 h, and then gradually cooled to 25° C. over 4-5 h. After stirring the reaction mixture for an additional 1 h at 25° C., the resulting residue was filtered, washed with methanol, and dried under vacuum for 30 min. Chiral HPLC of an aliquot of the product that was converted to the BOC derivative indicated 82.11% of the desired (R)-4-methylcyclohex-3-enamine hemi-dibenzoyl-D(+)-tartarate (7), and 17.82% of the corresponding S-isomer.

The crude product obtained above (~480 g) was treated with (+)-dibenzoyl-D-tartaric acid monohydrate (93.3 g) and methanol (2.9 L), and the resulting mixture was refluxed for 2 h, and then gradually cooled to 25° C. over 4-5 h. After stirring the reaction mixture for an additional 1 h at 25° C., the resulting residue was filtered, washed with methanol, and dried under vacuum for 30 min. The product thus obtained was further dried in air oven at 45-50° C. to furnish (R)-4-methylcyclohex-3-enamine hemi-dibenzoyl-D(+)-tartarate (7) (220.5 g, 28.5% yield, 97.81% purity by GC, melting point range: 205.2-206.3° C., OR: +110.0° (C=1% in acetic acid at 25° C.)); chiral HPLC indicated 86.88% of the desired R-isomer and 13.12% of the corresponding S-isomer.

(R)-tert-Butyl (4-methylcyclohex-3-en-1-yl)carbamate (8)

To a solution of NaOH (124 g) and water (1200 mL) at 10-20° C. was slowly added (R)-4-methylcyclohex-3-enamine hemi-dibenzoyl-D(+)-tartarate (7) (300 g) while keeping the temperature below 25° C. After stirring the reaction mixture for 15 min., the resulting free base was extracted from the aqueous layer using DCM (2×300 mL, 1×150 mL). The organic layers were combined, and the resulting solution (~850 mL) was treated with Boc anhydride (236.8 g) at 0-5° C. The reaction mixture was allowed to warm to 25° C., and stirred (≥2 h) at that temperature until HPLC indicated <1% unreacted intermediate (7). Upon completion of the reaction, as indicated by HPLC, water (230 mL) was added, and the mixture was stirred for 10 min. The organic layer was separated and washed with 2% aqueous citric acid solution (230 mL) followed with water (230 mL). DCM was distilled out at 30-40° C. under vacuum, and the resulting pale yellow mass was vacuum dried for 30 min. at 40-45° C. to furnish (R)-tert-butyl (4-methylcyclohex-3-en-1-yl)carbamate (8) (216 g, 98.91% yield based on HPLC, 98.36% purity by HPLC), which contained 14.85% of the corresponding S-isomer as indicated by chiral HPLC. The product thus obtained was taken in THF (437 mL), stirred for 10 min. to obtain a clear solution, and stored under an atmosphere of nitrogen for use in the next step.

tert-Butyl ((1R,3R,4R)-3-hydroxy-4-methylcyclohexyl)carbamate (9)

To a suspension of sodium borohydride (76.97 g) in THF (1290 mL) at 25° C. was slowly added (−)-α-pinene (582.07 g) over a period of 15 min. under an atmosphere of nitrogen. After cooling the reaction mixture to 0-5° C., boron trifluoride etherate (57%, 531.95 g) was added slowly over a period of 30-60 min. The reaction was allowed to warm to 25° C., stirred for 8 h, and then treated with the solution of (R)-tert-butyl (4-methylcyclohex-3-en-1-yl)carbamate (8) in THF prepared above (623 g, containing 215 g of (8)). The resulting reaction mixture was stirred (≥3 h) at 25° C. until HPLC indicated <1% unreacted intermediate (8). After cooling to 0-5° C., the reaction was quenched slowly by adding water over a period of 30-60 min., followed by subsequent addition of aqueous NaOH (244.15 g NaOH and 716 mL water) and a solution of 48% hydrogen peroxide (432.36 g). The reaction mixture was gradually warmed to 25° C. and stirred for 3 h, after which a solution of sodium thiosulfate (75 g sodium thiosulfate and 75 mL water) was added. After stirring for 30 min., a solution of citric acid (254 g of citric acid and 860 mL water) was added, and the mixture was stirred for an additional 30 min. after which ethyl acetate was added (1290 mL). After stirring for 10 min., the organic layer was separated and the aqueous fraction was extracted with ethyl acetate (2×430 mL). The organic layers were combined and the solvent was distilled out at 40-50° C. under vacuum. The resulting mass was vacuum dried for 1 h to afford quantitative yield of tert-butyl ((1R,3R,4R)-3-hydroxy-4-methylcyclohexyl)carbamate (9) (858 g crude), which was used for the next step without purification.

(1R,2R,5R)-5-amino-2-methylcyclohexanol hydrochloride (A)

A mixture of tert-butyl ((1R,3R,4R)-3-hydroxy-4-methylcyclohexyl)carbamate (9) from above (853 g, containing 233 g of (9)) and IPA-HCl (14% w/w solution; 699 mL) was stirred (≥2 h) at 25° C. until HPLC indicated <1% unreacted intermediate (9). The solvent was distilled out at 40-60° C. under vacuum. Fresh IPA (233 mL) was added at 40-45° C. and the solvent was again distilled out at 40-60° C. under vacuum. After degassing for 30 min. at 40-60° C., the resulting mass was treated with fresh IPA (699 mL) and the mixture was stirred under nitrogen at 30-35° C. for 30 min. and then at 0-5° C. for an additional 30 min. The solid product was filtered at 0-5° C. and washed with chilled IPA. The resulting product was dried under vacuum at 40-60° C. to afford ~70 g crude product, which contained ~96.49% of the desired RRR-isomer as indicated by chiral GC (other isomers were present as impurities in the amount of 2.06% (SSS isomer), 0.18% (SRR isomer), and 1.26% (RSS isomer)). IPA (3 L) was added and the resulting slurry was refluxed for 30 min. The mixture was gradually cooled to 70-75° C., and the undissolved impurity was filtered off and washed with IPA (140 mL). The solvent was distilled out at 40-60° C. to afford a white mass which was gradually cooled to 25° C. and then treated with water (31.5 mL) and acetonitrile (31.5 mL). The resulting mixture was heated at 75-80° C. for 10 min. to obtain a clear solution, which was then treated slowly with acetonitrile (574 mL) at 75-80° C. over a period of 1 h. After stirring for 15 min. at 75-80° C., the resulting mass was cooled to 0-5° C. over 2-3 h and stirred at that temperature for 30 min. The product was filtered under nitrogen at 0-5° C., and the solid cake was washed with chilled acetonitrile (70 mL) and dried under vacuum to afford the desired RRR isomer. The above process of precipitating the desired product out of a mixture of water and acetonitrile by addition of acetonitrile at 75-80° C. was repeated until chiral-GC indicated the presence of no more than 0.5% of any other single isomer (SSS, SRR and RSS isomer). The product thus obtained was further dried under vacuum at 40-60° C. to afford (1R,2R,5R)-5-amino-2-methylcyclohexanol hydrochloride (A) as a white solid (63 g, 37.4% yield, 100% purity by HPLC, melting point range: 244.0-245.5° C., SOR: −31.2° (C=1% in MeOH at 25° C.)); chiral GC indicated 99.83% of the desired RRR-isomer and 0.17% of the corresponding SSS-isomer.
$^1$H-NMR (D$_2$O) (400 MHz): δ 3.18-3.08 (m, 2H), 2.15-2.12 (m, 1H), 1.86-1.83 (m, 1H), 1.72-1.68 (m, 1H), 1.32-1.16 (m, 3H), 1.02-0.91 (m, 1H), 0.86-0.85 (d, 3H, J=6.4 Hz)

A number of references have been cited, the disclosures of which are incorporated herein by reference in their entirety.

What is claimed is:
1. A method for preparing a compound of formula (A),

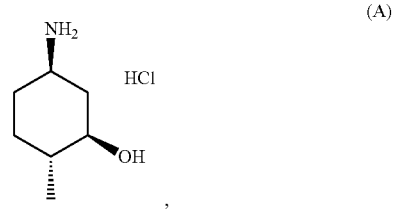

the method comprising the steps of:
(a) contacting a compound of formula (1),

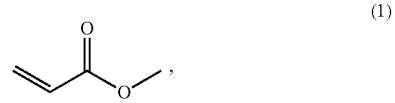

with a compound of formula (2),

in the presence of a Lewis Acid in a solvent to provide a compound of formula (3),

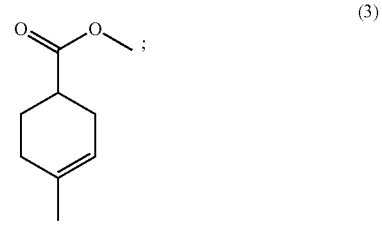

(b) contacting the compound of formula (3) of step (a) with an aqueous base to provide a compound of formula (4),

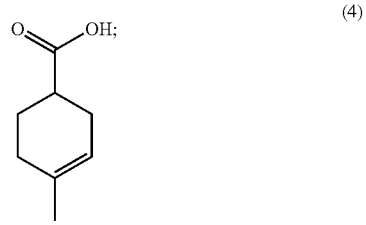

(c) contacting the compound of formula (4) of step (b) with DMF and a chlorinating agent in an organic solvent, followed by treatment of the resulting acid chloride derivative with aqueous ammonia to provide a compound of formula (5), (5)

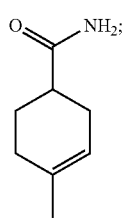

(d) contacting the compound of formula (5) of step (c) with an aqueous solution of NaOH and NaOCl to provide a compound of formula (6), (6)

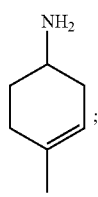

(e) contacting the compound of formula (6) of step (d) with (+)-dibenzoyl-D-tartaric acid monohydrate in a solvent to provide a compound of formula (7), (7)

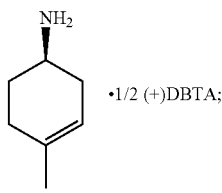

·1/2 (+)DBTA;

(f) contacting the compound of formula (7) of step (e) with an aqueous base, followed by treatment of the resulting free base with Boc$_2$O in an organic solvent to provide a compound of formula (8), (8)

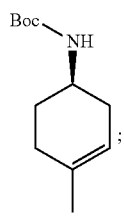

(g) contacting the compound of formula (8) of step (f) with a mixture of a reducing agent, a chiral auxiliary and a Lewis acid in a solvent, followed by treatment with an oxidant in the presence of a base to provide a compound of formula (9), (9)

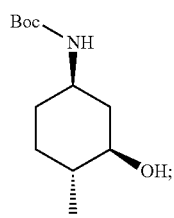

and (h) contacting the compound of formula (9) of step (g) with a solution of hydrochloric acid in a solvent to provide the compound of formula (A).

2. The method of claim 1, wherein the Lewis acid of step (a) is AlCl$_3$.

3. The method of claim 1, wherein the solvent of step (a) is DCM.

4. The method of claim 1, wherein the base of step (b) is NaOH.

5. The method of claim 1, wherein the chlorinating agent of step (c) is SOCl$_2$.

6. The method of claim 1, wherein the organic solvent of step (c) is DCM.

7. The method of claim 1, wherein the solvent of step (e) is MeOH.

8. The method of claim 1, wherein the base of step (f) is NaOH.

9. The method of claim 1, wherein the organic solvent of step (f) is DCM.

10. The method of claim 1, wherein the reducing agent of step (g) is NaBH$_4$.

11. The method of claim 1, wherein the chiral auxiliary of step (g) is α-pinene.

12. The method of claim 1, wherein the Lewis acid of step (g) is BF$_3$.Et$_2$O.

13. The method of claim 1, wherein the solvent of step (g) is THF.

14. The method of claim 1, wherein the oxidant of step (g) is H$_2$O$_2$.

15. The method of claim 1, wherein the base of step (g) is NaOH.

16. The method of claim 1, wherein the solvent of step (h) is IPA.

* * * * *